United States Patent [19]

Mita et al.

[11] Patent Number: 5,561,109
[45] Date of Patent: Oct. 1, 1996

[54] METHOD FOR THE HEALING OF WOUNDS CAUSED BY CORNEAL INJURY

[75] Inventors: Shiro Mita, Ashiya; Mitsushi Hikida, Takatsuki, both of Japan; Michel F. Degre, St Affrique, France

[73] Assignee: Santen Pharmaceutical Co., Ltd., Osaka, Japan

[21] Appl. No.: 426,635

[22] Filed: Apr. 21, 1995

Related U.S. Application Data

[63] Continuation of Ser. No. 64,037, filed as PCT/JP91/01539, Nov. 8, 1991, abandoned.

[30] Foreign Application Priority Data

Nov. 13, 1990 [JP] Japan ..................... 2-308036

[51] Int. Cl.$^6$ .............................. A61K 38/00; C07K 1/00
[52] U.S. Cl. .............................. 514/12; 514/21; 514/912; 514/915; 530/365; 530/832
[58] Field of Search ............................. 514/12, 21, 912, 514/915; 530/365, 832

[56] References Cited

U.S. PATENT DOCUMENTS 4,726,948  2/1988  Pripels et al. ..................... 424/94.4
4,745,100  5/1988  Gilbard et al. ..................... 514/12

FOREIGN PATENT DOCUMENTS 2-48534      2/1990   Japan.
2052979      2/1981   United Kingdom.
WO87/07838  12/1987   WIPO.

OTHER PUBLICATIONS

*Dorland's Illustrated Medical Dictionary*, Twenty-fifth Edition, Publisher-W. B. Saunders Company, 1974, p. 319.
Bannister et al, Enhanced Production Of Hydroxy Radicals By The Xanthine–Xanthine Oxidase Reaction In The Prsence Of Lactoferrin, Biochemica et Biophysica Acta, vol. 715, No. 1, (1982), pp. 116–120.
Exp. Eye Res. vol. 34, (1982) abstract.

*Primary Examiner*—Elizabeth C. Weimar
*Assistant Examiner*—Abdel A. Mohamed
*Attorney, Agent, or Firm*—Frishauf, Holtz, Goodman, Langer & Chick, P.C.

[57] ABSTRACT

A method for the healing of wounds caused by corneal injury, which includes administering to a mammalian patient in need thereof an effective wound healing amount of lactoferrin, lactoperoxidase or a combination of lactoferrin and lactoperoxidase as active ingredients, either alone or in admixture with at least one excipient.

14 Claims, No Drawings

METHOD FOR THE HEALING OF WOUNDS CAUSED BY CORNEAL INJURY

This application is a Continuation of application Ser. No. 08/064,037, filed May 7, 1993, now abandoned, which is the United States national phase application of International Application No. PCT/JP91/01539 filed Nov. 8, 1991.

TECHNICAL FIELD

This invention relates to therapeutic agents for corneal disorders, which contain lactoferrin and/or lactoperoxidase as (an) active ingredient(s).

BACKGROUND ART

Lactoferrin and lactoperoxidase are proteins existing in milk or tears of a human being, bovine, etc. and are known to have pharmacological effects such as an antibacterial effect and a proliferating effect of lymphocytes. (Japanese Unexamined Patent Publication 48534/1990, etc.)

However, there are few reports on their pharmacological effects in ophthalmology.

Therefore, the inventors studied to find new pharmacological effects of lactoferrin and lactoperoxidase and to apply them in the ophthalmological field. As the result, the inventors found that these compounds have stimulative effects on the proliferation of corneal keratocytes and are useful for treatment of corneal disorders.

DISCLOSURE OF THE INVENTION

This invention provides therapeutic agents for corneal disorders, which contain lactoferrin and/or lactoperoxidase as (an) active ingredient(s).

Lactoferrin and lactoperoxidase can be obtained generally from secretions, for example, milk and tears, of a human being or animals such as bovine. There is, therefore, no problem with the safety of these.

The inventors studied to find new pharmacological effects of lactoferrin and lactoperoxidase and to apply them in the ophthalmological field. As the result, the inventors found that these compounds have stimulative effects on the proliferation of corneal keratocytes and are useful for treatment of corneal disorders.

To examine the stimulative effects of lactoferrin and lactoperoxidase on proliferation of corneal keratocytes, the inventors tested these compounds using cultured rabbit corneal keratocytes in vitro and rabbit corneal alkali burn injury model in vivo.

As shown in the pharmacological test (hereinbelow) in detail, lactoferrin and lactoperoxidase significantly stimulated the proliferation of keratocytes.

The results indicate that lactoferrin and lactoperoxidase are useful for treatment of various corneal disorders such as corneal injury caused by ulceration, inflammation or ophthalmological surgery, etc.

Lactoferrin and/or lactoperoxidase can be administered orally or parenterally, but the preferable dosage form is eye drops.

For the purpose of this invention, lactoferrin or lactoperoxidase is administered alone or they are administered together.

The dosage of lactoferrin and/or lactoperoxidase is adjusted depending on symptom, age, dosage form, etc. In case of eye drops, the concentration (W/W) of lactoferrin and/or lactoperoxidase is 0.01–3.0% preferably.

Pharmaceutical preparations of lactoferrin and/or lactoperoxidase can be prepared by the known methods. In eye drops of lactoferrin and/or lactoperoxidase, usual excipient(s) such as isotonic agents, buffers, preservatives or pH adjusting agents can be combined.

BEST MODE FOR CARRYING OUT THE INVENTION

Examples of formulations are shown below.

| (FORMULATION EXAMPLES) | |
|---|---|
| formulation 1 | |
| lactoferrin | 0.5 g |
| sodium chloride | 0.9 g |
| sterile purified water | q.s. |
| total | 100 ml |
| formulation 2 | |
| lactoperoxidase | 0.5 g |
| sodium chloride | 0.9 g |
| sterile purified water | q.s. |
| total | 100 ml |
| formulation 3 | |
| lactoferrin | 0.25 g |
| lactoperoxidase | 0.25 g |
| sodium chloride | 0.9 g |
| sterile purified water | q.s. |
| total | 100 ml |

PHARMACOLOGICAL TEST

To examine the stimulative effects of lactoferrin and lactoperoxidase on proliferation of corneal keratocytes, the inventors tested these compounds using cultured rabbit corneal keratocytes in vitro and rabbit corneal alkali burn injury model in vivo.

1. Effect on Cultured Rabbit Corneal Keratocytes

Using cultured rabbit corneal keratocytes, the stimulative effects of lactoferrin and lactoperoxidase were examined by counting the uptake of $^3$H-thymidine into keratocytes.

Experimental Method

Cultured rabbit corneal keratocytes ($1 \times 10^4$ cells) were suspended in TC-199 medium (produced by GIBCO) containing 5 vol. % fetal calf serum. The keratocytes were cultured in a well of a 96-well flat bottom culture plate with lactoferrin or lactoperoxidase at 37° C. with 5% $CO_2$ in a $CO_2$ incubator. After 24 hr, the reaction mixture was plussed with $^3$H-thymidine (produced by AMERSHAM) and cultured at 37° C. for 24 hr. The proliferation of keratocytes were measured by liquid scintillation counter by counting radio activity of $^3$H-thymidine uptake to keratocytes.

Result

The results were shown in Table 1.

TABLE 1

Effects of lactoferrin and lactoperoxidase on the proliferation of cultured keratocytes in vitro

| Samples | | $^3$H-thymidine uptake ($\times 10^4$ dpm) | stimulation (%) |
|---|---|---|---|
| Control | | 13.16 | — |
| Lactoferrin | 30 μg/ml | 25.98 | 97.4 |
| | 100 μg/ml | 35.41 | 169.1 |
| | 300 μg/ml | 38.78 | 194.7 |
| | 1000 μg/ml | 42.37 | 222.0 |
| Lactoperoxidase | 30 μg/ml | 19.05 | 44.8 |
| | 100 μg/ml | 23.87 | 81.4 |
| | 300 μg/ml | 26.53 | 101.6 |
| | 1000 μg/ml | 26.57 | 101.9 |

As shown in Table 1, lactoferrin and lactoperoxidase significantly stimulated the proliferation of keratocytes in a dose-dependent manner.

2. Effect on Corneal Alkali Burn Injury

To confirm the effects of lactoferrin and lacotperoxidase in vivo, the inventors examined the effects of the compounds on rabbit corneal alkali burn injury.

Experimental Method

A filter disc (diameter: 5 mm) soaked in 1N NaOH was placed on the rabbit cornea for 1.5 minutes to elicit inflammation, and the cornea was washed with physiological saline. Just after the elicitation of inflammation, 0.5 wt. % eye drops of lactoferrin or lactoperoxidase dissolved in physiological saline was instilled 10 times per day at one hour intervals. After the continuous treatment for 13 days, the corneal keratocytes were examined histopathologicaly. As the control, physiological saline was instilled.

Result

The evaluation was made according to the following score table.

| | Score Table |
|---|---|
| 0 | No regeneration was observed. |
| 0.5 | Very slight regeneration was observed. |
| 1.0 | Slight regeneration was observed. |
| 2.0 | Moderate regeneration was observed. |
| 3.0 | Great regeneration was observed. |

The results were shown in Table 2, in which each score was represented by total scores of eight eyes.

TABLE 2

| test compound | score |
|---|---|
| control | 9.5 |
| lactoferrin | 12.5 |
| lactoperoxidase | 16.0 |

The results prove that lactoferrin and lactoperoxidase significantly accelerate the regeneration of corneal keratocytes in the in vivo test.

INDUSTRIAL APPLICABILITY

This invention provides excellent therapeutic agents for corneal disorders, which contain lactoferrin and/or lactoperoxidase as (an) active ingredient(s).

We claim:

1. A method for the healing of wounds caused by corneal injury in a mammalian patient, which comprises administering to the mammalian patient in need thereof an effective wound healing amount of lactoferrin and lactoperoxidase as active ingredients, either alone or in admixture with at least one excipient.

2. The method according to claim 1, wherein said excipients are sodium chloride and sterile purified water.

3. The method according to claim 1, wherein said lactoferrin and lactoperoxidase are instilled into an eye of said patient.

4. The method according to claim 3, wherein eye drops are instilled which contain said lactoferrin and lactoperoxidase, in a concentration from 0.01 to 3.0 (W/W) %.

5. A method for the healing of wounds caused by corneal injury in a mammalian patient which comprises administering to the mammalian patient in need thereof an effective corneal wound healing amount of an active ingredient, said active ingredient for corneal wound healing consisting essentially of lactoferrin, either alone or in admixture with at least one excipient.

6. The method according to claim 5, wherein said excipients are sodium chloride and sterile purified water.

7. The method according to claim 5, wherein said lactoferrin is instilled into an eye of said patient.

8. The method according to claim 7, wherein eye drops are instilled which contain said lactoferrin in a concentration from 0.01 to 3.0 (W/W) %.

9. A method of for the healing of wounds caused by corneal disorders injury in a mammalian patient, which comprises administering to the mammalian patient in need thereof an effective wound healing amount of lactoperoxidase as an active ingredient, either alone or in admixture with at least one excipient.

10. The method according to claim 9, wherein said excipients are sodium chloride and sterile purified water.

11. The method according to claim 9, wherein said lactoperoxidase is instilled into an eye of said patient.

12. The method according to claim 11, wherein eye drops are instilled which contain said lactoperoxidase in a concentration from 0.01 to 3.0 (W/W) %.

13. A method of healing corneal injury caused by ulceration, inflammation or ophthalmological surgery comprising instilling into an eye of a mammalian patient in need thereof an effective healing amount of an active ingredient selected from the group consisting of lactoferrin, lactoperoxidase and a combination of lactoferrin and lactoperoxidase, either alone or in admixture with a pharmaceutically acceptable diluent.

14. The method according to claim 13, wherein said active ingredient is instilled in the form of eye drops, said eye drops containing said active ingredient in a concentration of 0.01 to 3.0 (W/W) %.

* * * * *